United States Patent
Elder

(10) Patent No.: US 6,262,323 B1
(45) Date of Patent: Jul. 17, 2001

(54) POLYMERIZATION INHIBITION OF ISOPRENE

(75) Inventor: Sherri Elder, Sugar Land, TX (US)

(73) Assignee: Baker Hughes Incorporated, Houston, TX (US)

(*) Notice: Subject to any disclaimer, the term of this patent is extended or adjusted under 35 U.S.C. 154(b) by 0 days.

(21) Appl. No.: 09/460,955

(22) Filed: Dec. 14, 1999

(51) Int. Cl.[7] ................................................. C07C 7/20
(52) U.S. Cl. ............................... 585/5; 585/3; 585/4
(58) Field of Search .......................... 585/3, 5, 4

(56) References Cited

U.S. PATENT DOCUMENTS

| | | | | |
|---|---|---|---|---|
| 4,929,778 | * | 5/1990 | Roling | 585/5 |
| 5,396,004 | * | 3/1995 | Arhancet et al. | 585/5 |
| 5,396,005 | * | 3/1995 | Arhancet | 585/5 |
| 5,416,258 |   | 5/1995 | Arhancet et al. | 585/3 |
| 5,446,220 | * | 8/1995 | Arhancet | 585/5 |
| 5,510,547 | * | 4/1996 | Aehancet et al. | 585/5 |
| 5,648,574 | * | 7/1997 | Arhancet et al. | 585/5 |

OTHER PUBLICATIONS

Chemical Abstract 109:192574, 1988.
Chemical Abstract 100:192330, 1984.
Chemical Abstract 95:170696, 1981.
Chemical Abstract 94:176449, 1981.

* cited by examiner

Primary Examiner—Jacqueline V. Howard
(74) Attorney, Agent, or Firm—Madan, Mossman & Sriram P.C.

(57) ABSTRACT

It has been discovered that the polymerization of diene compounds, such as isoprene, may be inhibited by the addition of a composition that contains a at least one phenylenediamine, at least one sterically hindered phenol, and at least one hydroxylamine. This three-component composition exhibits synergistically improved results over the use of the components individually or in paired combinations. In one preferred embodiment, the polymerization inhibiting composition includes phenylenediamine (PDA), butylated hydroxytoluene (BHT), and N,N'-diethylhydroxylamine (DEHA).

12 Claims, 1 Drawing Sheet

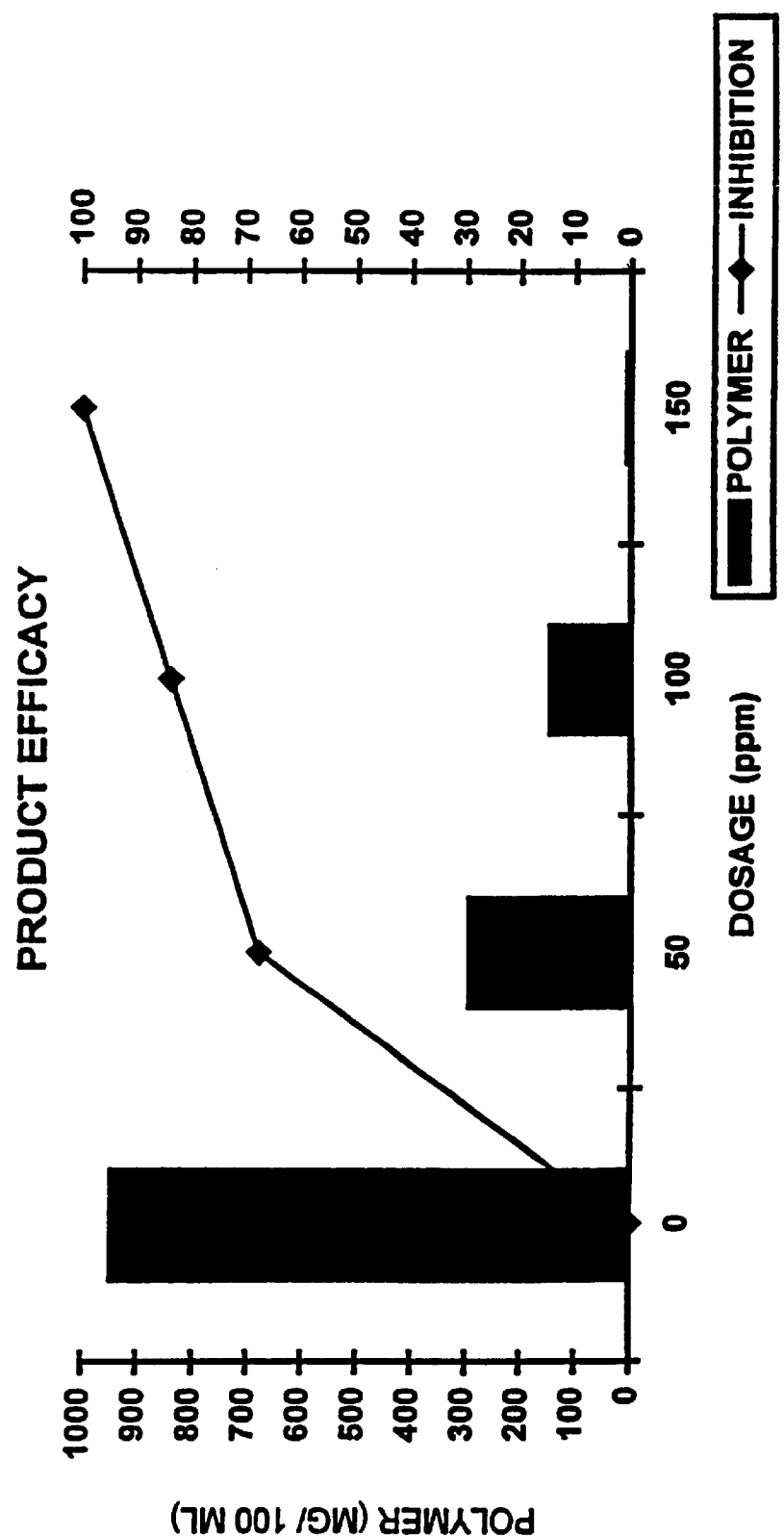

POLYMERIZATION INHIBITION OF ISOPRENE

FIELD OF THE INVENTION

The present invention relates to methods and compositions for inhibiting the polymerization of vinyl unsaturated monomers, and more particularly relates, in one embodiment, to methods and compositions for inhibiting the polymerization of dienes such as isoprene.

BACKGROUND OF THE INVENTION

It is well known that undesirable and costly polymerization is a significant problem during the manufacturing of various unsaturated monomers, particularly vinyl aromatic compounds, such as reactive dienes, specifically isoprene. In the purification of isoprene, reboilers on the extractive distillation absorber and stripper towers, and other equipment can experience fouling due to the presence of small oligomers (dimers/trimers/tetramers) of isoprene and cyclopentadiene, and large molecular weight free-radical polymers. The free-radical polymers are mixtures of linear and cross-linked isoprene and polymerized dimers.

Many kinds of inhibitors have been used in the past to minimize this problem. For instance, inhibitors such as diethylhydroxylamine, phenyl-p-phenylenediamines, tert-butyl catechol, and phenothiazine have been used to control polymer formation. During the early 1980s, compounds selected from the groups called alkyl-substituted di-nitro-phenols and nitroso-phenols found widespread use in the styrene industry. However, because such compounds also functioned as insecticides or were dangerous to handle, their use has been discouraged by environmental and government agencies.

It would be desirable if a composition and method could be devised to overcome some of the problems of the commercial polymerization inhibitors, and in particular to improve upon the performance of such prior inhibitors.

SUMMARY OF THE INVENTION

Accordingly, it is an object of the present invention to provide a method and composition to effectively inhibit the polymerization of dienes such as isoprene.

It is another object of the present invention to provide a method and composition to effectively inhibit the polymerization of dienes that is more effective than using antioxidants and antipolymerants independently.

Still another object of the invention is to permit use of a composition to effectively inhibit the polymerization of isoprene that has reduced environmental concerns compared to some previous polymerization inhibitors.

In carrying out these and other objects of the invention, there is provided, in one form, a method for inhibiting the polymerization of a diene involving adding an effective amount thereto of a mixture including at least one phenylenediamine, at least one sterically hindered phenol, and at least one hydroxylamine.

BRIEF DESCRIPTION OF THE DRAWING

The FIGURE is a chart of the product efficacy of a polymerization inhibiting mixture of the invention at various doses where the proportion of polymer is shown by the bars measured against the left vertical axis, and where the percentage of polymer inhibition is shown by the line measured against the right vertical axis.

DETAILED DESCRIPTION OF THE INVENTION

It is known that an antioxidant and an antipolymerant have been used separately to effectively treat reactive dienes. However, a synergy has been observed between the co-use of antioxidants of the sterically hindered phenol type and the phenylenediamine type with an antipolymerant (polymerization inhibitor) of the hydroxylamine type.

Thus, the invention is a synergistic blend of at least two antioxidants and at least one antipolymerant to inhibit polymerization in the purification of reactive dienes, particularly isoprene. While the antioxidants and the antipolymerant have been used separately to treat fouling in reactive diene separation, it is not believed that the use of at least two antioxidants and at least one antipolymerant to inhibit polymerization of dienes is known, much less known that this combination performs synergistically. The synergistic results indicate that because the mixture of this invention works better than the components separately or in paired combination, the better performance requires less chemical treatment for the same beneficial effect.

In the inventive mixture or blend of the invention, the two antioxidants may be selected from the group including, but not necessarily limited to, phenylenediamines such as p- or m-phenylenediamine itself (PDA); N,N'-bis-sec-butyl-p-phenylenediamine; N,N'-diphenylphenylenediamine; N,N,N',N'-tetramethyl-p-phenylenediamine; N,N'-bis-(1,4-dimethylpentyl)-p-phenylenediamine; N-phenyl-N'-(1,4-dimethylpentyl)-p-phenylenediamine; N-phenyl-N'-(1,3-dimethylbutyl)-p-phenylenediamine; N-phenyl-N-cyclohexyl-p-phenylenediamine; N,N'-dinaphthyl-p-phenylenediamine; N-isopropyl-N'-phenyl-p-phenylenediamine; N-aminoalkyl-N'-phenyl-p-phenylenediamine; N-(2-methyl-2-aminopropyl)-N'-phenyl-p-phenylenediamine; phenyl-β-isopropyl-aminophenylamine; p-hydroxydiphenylamine; p-hydroxylphenyl-P-naphthylamine; β-naphthalenediamine; and hindered phenolic compounds, such as o- and p-sec-butylphenol; 2,4-di-sec-butylphenol; 2,6-di-sec-butylphenol; 2,4,6-tri-sec-butylphenol; 2,4,6-trimethylphenol; butylated hydroxytoluene (BHT, also known as 2,6-tert-butyl-4-methylphenol and 2,6-tert-butyl-p-cresol); 2,6-dibutyl-4-methylphenol; hydroquinone; monomethylether of hydroquinone (MEHQ); β-naphthoquinone; N-phenyl-p-aminophenol; and mixtures thereof. Preferably, at least one phenylenediamine and at least one hindered phenolic compound are used together. It is particularly preferred, in one non-limiting embodiment of the invention to use PDA and BHT together.

Further, in one embodiment of the invention, the antipolymerant is selected from the group including, but not necessarily limited to, hydroxylamines such as N,N'-dialkylhydroxylamines, particularly N,N'-diethylhydroxylamine (DEHA), N,N'-bis-(hydroxypropyl) hydroxylamine, and mixtures thereof. It is preferred, in one non-limiting embodiment of the invention to use DEHA together with the antioxidants.

A solvent may be present in the polymerization inhibiting mixture of this invention. Suitable solvents include, but are not necessarily limited to, dimethylformamide (DMF), acetonitrile (ACN), kerosene, heavy aromatic naphtha, and the like.

In one non-limiting embodiment of the invention, the proportion of the phenylenediamine ranges from about 1 to about 30 wt. % of the total polymerization inhibiting mixture, the sterically hindered phenol ranges from about 1 to about 30 wt. %; and the hydroxylamine ranges from about 1 to about 40 wt. %. In a preferred embodiment of the invention, the proportion of the phenylenediamine ranges from about 5 to about 15 wt. %, the sterically hindered phenol ranges from about 5 to about 15 wt. %; and the hydroxylamine ranges from about 10 to about 20 wt. %; based on the total polymerization inhibiting mixture.

A number of factors affect the effective amount of the polymerization inhibiting mixture of this invention that would be useful to inhibit the polymerization of a diene compound, including, but not necessarily limited to, the nature of the compound, the concentration of the compound, the temperature and pressure environment of the compound, the nature of the particular components in the polymerization inhibiting mixture used, the ratio of the components, and the like. The invention is not limited to inhibiting polymerization of diene in particular temperature and pressure environments, for instance, purification processes. Nevertheless, some general guidelines as to the effective proportion of the polymerization inhibiting mixture in the diene compound may be given.

For instance, the amount of polymerization inhibiting mixture in the diene compound may range from about 5 to about 1,000 ppm, preferably from about 25 to about 150 ppm, in the plant under dynamic conditions, based on the total amount of diene compound.

The components of the multiple component composition may be simply mixed together. They may be mixed together in a single composition prior to addition to the diene compound, although they may also be added to the diene compound separately as well.

The invention will be further illustrated with respect to specific examples, which are not intended to limit the invention, but rather to more fully describe it.

EXAMPLES 1–3

Three isoprene polymerization inhibitor candidates were injected into crude isoprene at 5 ppm dosages in an isoprene purification unit. The amount of unwashed polymer recovered and the percentage of polymerization inhibition achieved are reported in Table I. The three candidates were:

Comparative Example 1—a proprietary blend of DEHA and TBC.

Comparative Example 2—a proprietary commercial polymerization inhibitor.

Inventive Example 3—15 wt. % BHT; 20 wt. % DEHA; 15 wt. % PDA (specifically bis-sec-butyl-p-phenylenediamine, sold as UOP5); and 50 wt. % DMF solvent.

TABLE I

Candidate Product Testing on Crude Isoprene

| Ex. No. | Dosage (ppm) | Unwashed Polymer (mg/100 ml) | % Inhibition |
|---|---|---|---|
| Blank | — | 266.3 | — |
| 1 | 5 | 56.4 | 100 |
| 2 | 5 | 62.0 | 90 |
| 3 | 5 | 57.2 | 100 |

EXAMPLE 4

The inventive composition of Example 3 was tested in crude isoprene at various doses. The results are presented in Table II and plotted in the FIGURE.

TABLE II

Candidate Product Testing on Crude Isoprene

| Ex. 3 Dosage (ppm) | Unwashed Polymer (mg/100 ml) | % Inhibition |
|---|---|---|
| Blank (0) | 946.0 | — |
| 50 | 296.4 | 68.8 |
| 100 | 148.0 | 84.0 |
| 150 | 6.8 | 99.5 |

EXAMPLES 5–10

With further testing, it was surprisingly discovered that polymerization formulations of the invention (Examples 7 and 8) gave better results in inhibiting polymerization of crude isoprene than the same components alone or in paired combination. Results are presented in Table III.

TABLE III

Testing on Crude Isoprene Yielding Synergistic Results

| Ex. No. | Composition | Dosage (ppm) | % Inhibition |
|---|---|---|---|
| 5 | DEHA/TBC | 100 | 22.4 |
| 6 | PDA | 100 | 67.5 |
| 7 | DEHA/PDA/TBC | 100 | 99 |
| 8 | DEHA/PDA/BHT | 75 | 99 |
| 9 | PDA/TBC | 100 | 60 |
| 10 | PDA/BHT | 100 | 72 |

EXAMPLES 11–17

With further testing, it was surprisingly discovered that polymerization formulations of the invention (Examples 16 and 17) gave better results in inhibiting polymerization of crude isoprene than the same components alone or in paired combination. Results are presented in Table IV.

TABLE IV

Testing on Crude Isoprene Yielding Synergistic Results

| Ex. No. | Additive Composition | Dosage (ppm) | % Inhibition |
|---|---|---|---|
| 11 | PDA (UOP5) | 25 | 0 |
| 12 | BHT | 25 | 8 |
| 13 | DEHA | 25 | 51 |
| 14 | PDA + DEHA | 25 + 25 | 63 |
| 15 | BHT + DEHA | 25 + 25 | 60 |
| 16 | PDA + BHT + DEHA | 25 + 25 + 25 | 100 |
| 17 | PDA + BHT + DEHA | 8.3 + 8.3 + 8.3 (= 25) | 55 |

As can be seen in the data, when only two components are combined the effects are additive. If the effects remained additive, adding PDA to the two component combination would not show any increase. The results indicate, however, that the addition is synergistic as the % inhibition increases to 100%.

In the foregoing specification, the invention has been described with reference to specific embodiments thereof, and has been demonstrated as effective in providing a composition for inhibition of polymerization of diene compounds, such as isoprene. However, it will be evident that various modifications and changes can be made thereto without departing from the broader spirit or scope of the invention as set forth in the appended claims. Accordingly, the specification is to be regarded in an illustrative rather than a restrictive sense. For example, specific phenylenediamines, hydroxylamines and hindered phenolic compounds, and/or combinations of certain compounds, other than those specifically tried, in other proportions or added in different ways, falling within the claimed parameters, but not specifically identified or tried in a particular composition to improve the polymerization inhibition herein, are anticipated to be within the scope of this invention.

What is claimed is:

1. A method for inhibiting the polymerization of a diene comprising adding an effective amount thereto of a mixture comprising:
    at least one phenylenediamine:
    at least one sterically hindered phenol that is not a di-nitro-phenol; and
    at least one hydroxylamine.

2. The method of claim 1 where in the adding, the amount of mixture based on the amount of diene ranges from about 5 to about 1,000 ppm.

3. The method of claim 1 where in the adding, the mixture further comprises:
    from about 1 to about 30 wt. % of phenylenediamine;
    from about 1 to about 30 wt. % of sterically hindered phenol; and
    from about 1 to about 40 wt. % of hydroxylamine.

4. The method of claim 1 where the diene is isoprene.

5. A method for inhibiting the polymerization of a diene comprising adding an effective amount thereto of a mixture comprising:
    phenylenediamine (PDA):
    butylated hydroxytoluene (BHT); and
    N,N'-diethylhydroxylamine (DEHA).

6. The method of claim 5 where in the adding, the amount of mixture based on the amount of isoprene ranges from about 5 to about 1,000 ppm.

7. The method of claim 5 where in the adding, the mixture further comprises:
    from about 1 to about 30 wt. % of phenylenediamine;
    from about 1 to about 30 wt. % of sterically hindered phenol; and
    from about 1 to about 40 wt. % of hydroxylamine.

8. The method of claim 5 where the diene is isoprene.

9. A diene polymerization inhibiting composition comprising:
    at least one phenylenediamine:
    at least one sterically hindered phenol that is not a di-nitro-phenol; and
    at least one hydroxylamine.

10. The diene polymerization inhibiting composition of claim 9 where:
    the proportion of phenylenediamine ranges from about 1 to about 30 wt. %
    the proportion of sterically hindered phenol ranges from about 1 to about 30 wt. %; and
    the proportion of hydroxylamine ranges from about 1 to about 40 wt. %.

11. A diene polymerization inhibiting composition comprising:
    phenylenediamine (PDA):
    butylated hydroxytoluene (BHT); and
    N,N'-diethylhydroxylamine (DEHA).

12. The diene polymerization inhibiting composition of claim 11 where:
    the proportion of PDA ranges from about 1 to about 30 wt. %;
    the proportion of BHT ranges from about 1 to about 30 wt. %; and
    the proportion of DEHA ranges from about 1 to about 40 wt. %.

* * * * *